US007850913B2

(12) United States Patent
Yanagimachi

(10) Patent No.: US 7,850,913 B2
(45) Date of Patent: Dec. 14, 2010

(54) METHOD OF PARAFFIN-PENETRATION TREATMENT FOR TISSUE PREPARATION AND APPARATUS FOR THE TREATMENT

(75) Inventor: Akira Yanagimachi, Chikuma (JP)

(73) Assignees: Sakura Seiki Co., Ltd., Chikuma-Shi, Nagano (JP); Sakura Finetek Japan Co., Ltd., Tokyo (JP)

( * ) Notice: Subject to any disclaimer, the term of this patent is extended or adjusted under 35 U.S.C. 154(b) by 120 days.

(21) Appl. No.: 12/087,341

(22) PCT Filed: Dec. 28, 2006

(86) PCT No.: PCT/JP2006/326186

§ 371 (c)(1),
(2), (4) Date: Jul. 2, 2008

(87) PCT Pub. No.: WO2007/077911

PCT Pub. Date: Jul. 12, 2007

(65) Prior Publication Data

US 2009/0004640 A1 Jan. 1, 2009

(30) Foreign Application Priority Data

Jan. 6, 2006 (JP) ............................. 2006-001407

(51) Int. Cl.
*G01N 21/00* (2006.01)
(52) U.S. Cl. .............................. 422/63; 422/64; 422/65; 422/66; 422/67; 422/99; 422/100
(58) Field of Classification Search ............. 422/63–67, 422/99–100
See application file for complete search history.

(56) References Cited

U.S. PATENT DOCUMENTS

| 3,227,130 A | * | 1/1966 | Weiskopf ..................... 118/697 |
| 2005/0147538 A1 | * | 7/2005 | Williamson et al. ......... 422/102 |
| 2005/0226770 A1 | | 10/2005 | Allen et al. |

FOREIGN PATENT DOCUMENTS

| JP | 4-131735 A | 5/1992 |
| JP | 2001-133371 A | 5/2001 |
| JP | 2006-500584 A | 1/2006 |
| JP | 2006-500585 A | 1/2006 |

* cited by examiner

*Primary Examiner*—Jyoti Nagpaul
(74) *Attorney, Agent, or Firm*—Birch, Stewart, Kolasch & Birch, LLP

(57) ABSTRACT

The present invention provides a paraffin-penetration treatment method for a tissue preparation, which is capable of enabling sufficient penetration of paraffin even into a tissue preparation, into which paraffin can hardly penetrate by a conventional paraffin-penetration treatment method. When the penetration of the paraffin into the tissue preparation is performed by immersing the tissue preparation in molten paraffin after a dehydrating and a degreasing treatments, the method comprises the steps of: immersing the tissue preparation in the molten paraffin so as to allow the paraffin to penetrate into the tissue preparation; cooling the tissue preparation so as to solidify the paraffin having penetrated thereinto; and immersing the tissue preparation in the molten paraffin again so as to melt the paraffin having penetrated thereinto, and the above described solidification treatment and melting treatment are conducted at least once for one tissue preparation.

5 Claims, 1 Drawing Sheet

METHOD OF PARAFFIN-PENETRATION TREATMENT FOR TISSUE PREPARATION AND APPARATUS FOR THE TREATMENT

FIELD OF TECHNOLOGY

The present invention relates to a method of a paraffin-penetration treatment for a tissue preparation and an apparatus for the method, more precisely relates to a method of a paraffin-penetration treatment for a tissue preparation, in which a dehydrated and degreased tissue preparation is immersed in molten paraffin so as to allow the paraffin to penetrate into the tissue preparation, and an apparatus for the method.

BACKGROUND TECHNOLOGY

For example, as described in Patent Document 1, a tissue preparation for microscopic observation, e.g., pathological examination, is produced by the steps of: immersing a tissue preparation, which has been obtained from a human body, etc., in formalin so as to fix the tissue preparation; performing a dehydrating treatment, a degreasing treatment and a paraffin-penetration treatment; and embedding the tissue preparation, into which the paraffin has penetrated, (forming the tissue preparation into a block) in paraffin. Then, the tissue preparation embedded in the paraffin is sliced to form sliced pieces, and the sliced pieces are stained for microscopic observation.

In the above described steps for producing the tissue preparation, the paraffin-penetrated tissue preparation, in which the paraffin exists in the molten state, is embedded in paraffin.

Patent Document 1: Japanese Patent Kokai Gazette No. 2001-133371

DISCLOSURE OF THE INVENTION

In the above described process, if the paraffin sufficiently penetrates into tissues of the tissue preparation, the paraffin-embedded tissue preparation can be smoothly sliced, so that the sliced pieces have no cracks, etc. and they can be suitably used for microscopic observation.

However, paraffin cannot sufficiently penetrate into some tissue preparations, e.g., skin, ischiadic nerve, by the conventional paraffin-penetration treatment method. If paraffin insufficiently penetrates into tissues of a tissue preparation, it is difficult to slice the paraffin-embedded tissue preparation and the sliced pieces will have cracks. Therefore, the sliced pieces cannot be used for microscopic observation.

An object of the present invention is to provide a method of a paraffin-penetration treatment for a tissue preparation, which is capable of enabling sufficient penetration of paraffin even into a tissue preparation, into which paraffin can hardly penetrate by the conventional method, and an apparatus for performing said method.

The inventor of the present invention has studied to solve the above described problems and found that paraffin could sufficiently penetrate into a tissue preparation, into which paraffin could hardly penetrate by the conventional method, by performing a solidification treatment, in which the tissue preparation, into which paraffin had penetrated, was cooled so as to solidify the paraffin therein, and a melting treatment, in which the tissue treatment was immersed in molten paraffin again so as to melt the solidified paraffin, at least once for one tissue preparation, so that he reached the present invention.

Namely, the method of a paraffin-penetration treatment for a tissue preparation, in which a dehydrated and degreased tissue preparation is immersed in molten paraffin so as to allow the paraffin to penetrate into the tissue preparation, comprises the steps of: immersing the tissue preparation in the molten paraffin so as to allow the paraffin to penetrate into tissues of the tissue preparation; cooling the tissue preparation so as to solidify the paraffin having penetrated thereinto; and immersing the tissue preparation in the molten paraffin again so as to melt the solidified paraffin having penetrated thereinto, wherein said solidification treatment and said melting treatment are conducted at least once for one tissue preparation.

Further, the apparatus for a paraffin-penetration treatment, in which a dehydrated and degreased tissue preparation is immersed in molten paraffin so as to allow the paraffin to penetrate into the tissue preparation, comprises: penetration means for immersing the tissue preparation in the molten paraffin so as to allow the paraffin to penetrate into the tissue preparation; solidification means for cooling and solidifying the paraffin, which has been allowed to penetrate into the tissue preparation by the penetration means; and a controller for controlling the penetration means and the solidification means so as to perform the solidification treatment, in which the tissue preparation is cooled and the molten paraffin which has been penetrated inside the tissue is solidified, and the melting treatment, in which the tissue preparation is immersed in the molten paraffin again so as to melt the solidified paraffin having penetrated into the tissue preparation, wherein the solidification treatment and the melting treatment are conducted at least once for one tissue preparation.

In the present invention, the paraffin having penetrated into the tissue preparation may be solidified in a state in which the tissue preparation is separated from the molten paraffin, so that a cooling rate of the tissue preparation can be improved.

Further, the paraffin having penetrated into the tissue preparation is solidified at room temperature or below, e.g., 0° C. or below, so that the tissue preparation, which has been embedded in paraffin after performing the paraffin-penetration treatment, can be easily sliced, and good sliced pieces, which can be suitably used for microscopic observation, can be produced.

Note that, the paraffin-penetration treatment of the present invention does not include an embedding process, in which the tissue preparation treated by the paraffin-penetration treatment method is embedded in paraffin so as to form into a block.

In case of slicing some tissue preparations, e.g., skin, ischiadic nerve, it is very difficult to slice said tissue preparations, which have been treated by mere paraffin-penetration and embedded in paraffin to form into blocks, and their sliced pieces cannot be used for microscopic observation.

On the other hand, in the present invention, the tissue preparations, e.g., skin, ischiadic nerve, which have been treated by the above described paraffin-penetration treatment and embedded in paraffin, can be sufficiently sliced, and the sliced pieces can be used for microscopic observation.

Even tissue preparations, which cannot be easily sliced after being treated by the conventional paraffin-penetration treatment method and being embedded in paraffin, can be sliced after being treated by the paraffin-penetration treatment method of the present invention and being embedded in paraffin, but the detailed reason is not found.

Thus, the inventor thinks that the tissue preparations, e.g., skin, ischiadic nerve, include much fat, so they cannot be sufficiently degreased by the conventional degreasing treatment. It is confirmed by the fact that tissue preparations, e.g., skin, ischiadic nerve, can be sliced by performing the degreasing treatment for a long time and performing the conventional paraffin-penetration treatment.

On the other hand, in the present invention, the tissue preparation is immersed in the molten paraffin so as to allow the paraffin to penetrate into tissues of the tissue preparation, the tissue preparation is cooled so as to once solidify the paraffin having penetrated thereinto, and then the tissue preparation is immersed in the molten paraffin again so as to melt the solidified paraffin having penetrated thereinto.

By conducting the solidification treatment and the melting treatment at least once for one tissue preparation, the solidified paraffin having penetrated into the tissues of the tissue preparation is melted. At that time, volume of the paraffin in cells is expanded and fat left in the cells is discharged outside, so that the cells in the fat is fully replaced by the paraffin.

As a result, the cells of the tissue preparation are fully filled with the paraffin by performing the paraffin-penetration treatment method of the present invention, so that even the tissue preparations including much fat, e.g., skin, ischiadic nerve, can be sufficiently sliced after being embedded in paraffin and good sliced pieces can be obtained.

In the present invention, a prolonged degreasing treatment is not required prior to the paraffin-penetration treatment, so that efficiency of treating tissue preparations can be improved.

OPTIMUM EMBODIMENTS OF THE INVENTION

Figure 1:
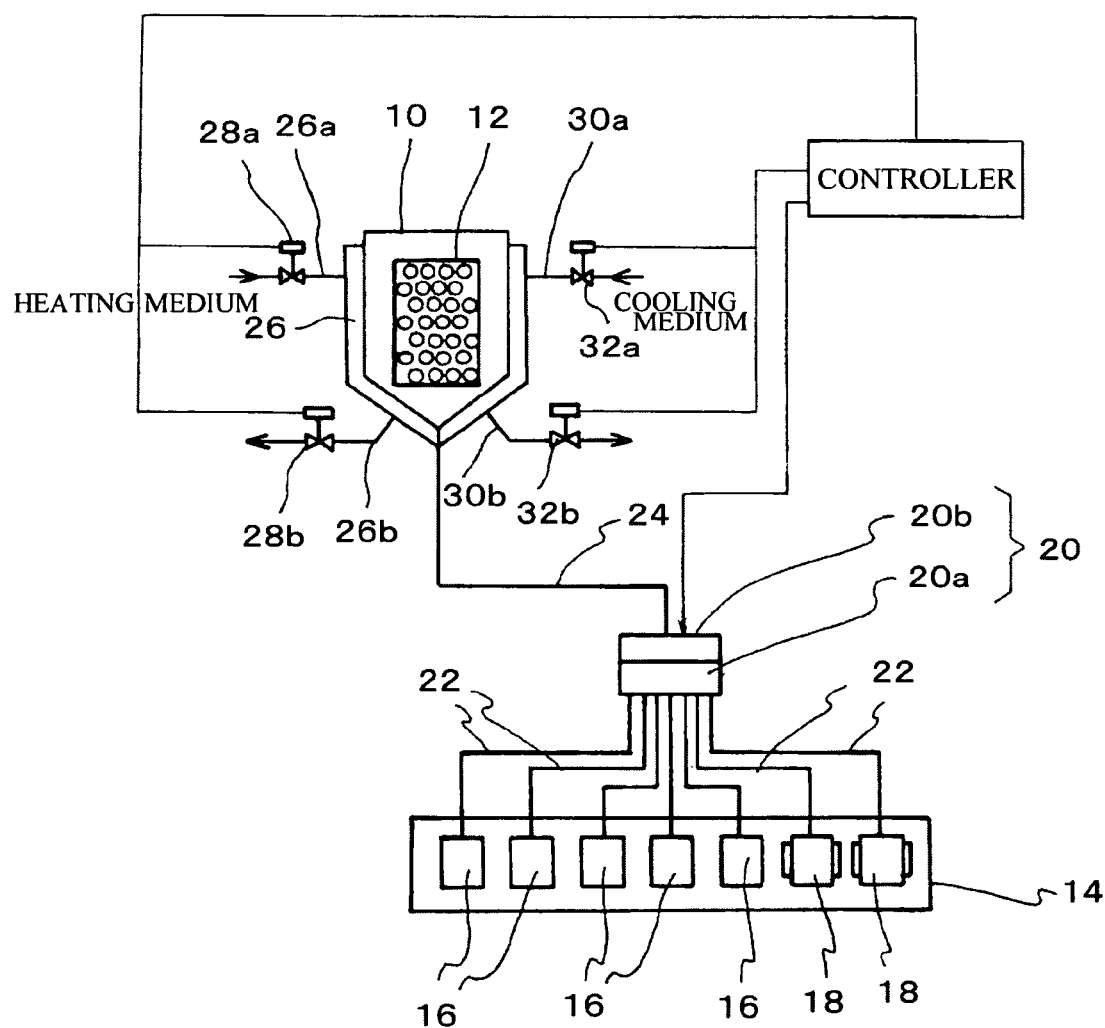
FIG. 1 is an explanation view showing an embodiment of the apparatus of the present invention, which performs the paraffin-penetration treatment method of the present invention.

The apparatus of the present invention, which performs the paraffin-penetration treatment method of the present invention, is shown in FIG. 1. The paraffin-penetration treatment apparatus shown in FIG. 1 is a one-tub type apparatus, which has one closed treatment tub 10 whose outer circumferential face is covered with a jacket 26. A basket 12, in which tissue preparations are stored, is accommodated in the treatment tub 10.

Solutions, i.e., ethanol and xylene, for treating the tissue preparations stored in the basket 12 accommodated in the treatment tub 10 are stored in tanks 16, 16 . . . accommodated in an accommodating section 14; molten paraffin, whose melting point is about 60° C., is stored in tanks 18 and 18 equipped with heaters. Tubes 22, 22 . . . whose front ends are respectively connected to the tanks 16, 16 . . . and the tanks 18 and 18 equipped with the heaters, are connected to a selection valve 20, and the selection valve 20 and the treatment tub 10 are connected by a tube 24. The selection valve 20 is constituted by a valve seat 20a, in which a plurality of tank ports are formed, and a valve plate 20b, in which a tub port is formed. The other ends of the tubes 22, 22 . . . are respectively connected to the tank ports of the valve seat 20a.

The tanks storing the solutions are connected to the treatment tub 10 by the selection valve 20, so that a desired solution can be supplied to the treatment tub 10. On the other hand, when the solution in the treatment tub 10 is discharged, the tank to which the solution is discharged from the treatment tub 10 is selected by the selection valve 20, so that the solution in the treatment tank 10 can be discharged to the selected tank.

A cooling medium can be supplied to the jacket 26 covering the outer circumferential face of the treatment tub 10 via an electromagnetic valve 32a provided to a pipe 30a; the cooling medium can be discharged from the jacket 26 via an electromagnetic valve 32b provided to a pipe 30b. Further, a heating medium can be supplied to the jacket 26 of the treatment tub 10 via an electromagnetic valve 28a provided to a pipe 26a; the heating medium can be discharged from the jacket 26 via an electromagnetic valve 28b provided to a pipe 26b.

Since the selection valve 20 and the electromagnetic valves 28a, 28b, 32a and 32b are controlled by a controller, an inner space of the treatment tub 10 can be set at desired temperature by controlling to supply the cooling medium and the heating medium to and discharge the same from the jacket 26.

The paraffin-penetration treatment of the present invention can be performed with tissue preparations obtained from a human body by the paraffin-penetration treatment apparatus shown in FIG. 1. Ethanol is stored in some of the tanks 16, 16 . . . installed in the apparatus. Amounts of water in a part of the tanks 16, 16 . . . storing ethanol may be gradually reduced. In this case, amounts of water in the rest tanks 16, 16 . . . of the tanks 16, 16 . . . storing ethanol are substantially zero. Further, xylene is stored in the tanks 16, 16 . . . other than the tanks 16, 16 . . . storing ethanol.

Molten paraffin is stored in the tanks 18, 18 . . . , which have the heaters and which are separated from the tanks 16, 16 . . . .

The obtained tissue preparations are firstly immersed in formalin and fixed, and then they are stored in the basket 12 and accommodated in the treatment tub 10 so as to perform an ordinary dehydrating treatment and an ordinary degreasing treatment. While executing these steps, the electromagnetic valves 28a, 28b, 32a and 32b are closed, so that no cooling medium and no heating medium are supplied to the jacket.

Firstly, the controller sends a signal to the selection valve 20 so as to supply ethanol from the first selected tank 16 of the tanks 16, 16 . . . storing ethanol to the treatment tub 10, and the ethanol is discharged after a lapse of a prescribed time period. Further, ethanol is supplied from other tanks 16, 16 . . . in prescribed order, as well, so that moisture in the tissue preparations can be replaced with ethanol.

Next, the controller sends a signal to the selection valve 20 so as to supply xylene from the first selected tank 16 of the tanks 16, 16 . . . storing xylene to the treatment tub 10, in which the ethanol treatment has been completed, and the xylene is discharged after a lapse of a prescribed time period, and then xylene is supplied to the treatment tank 10 from the next selected tank 16. By supplying the xylene to the treatment tub 10 from the tanks, 16, 16 . . . in prescribed order, the ethanol in the tissue preparations can be replaced with xylene.

Further, the controller sends a signal to the selection valve 20 so as to supply molten paraffin to the treatment tub 10 from the first selected tank 18 of the tanks 18 and 18 equipped with the heaters, in which the xylene treatment has been completed, the molten paraffin is discharged after a lapse of a prescribed time period, and then molten paraffin is supplied to the treatment tank 10 from the other tank 18 so as to replace the xylene in the tissue preparations with molten paraffin.

While immersing the tissue preparation in the molten paraffin, temperature of the inner space of the treatment tub 10 is maintained at melting point of paraffin or above. Thus, the controller may open the electromagnetic valves 28a and 28b so as to supply the heating medium to the jacket.

After replacing moisture in the tissue preparations with paraffin and discharging the molten paraffin from the treatment tub 10, the controller sends signals to close the electromagnetic valves 28a and 28b and open the electromagnetic valves 32a and 32b, so that the cooling medium is supplied to the jacket 26 of the treatment tub 10 and the treatment tub 10 is cooled. By cooling the treatment tub 10, the paraffin having penetrated into the tissue preparations is solidified.

Next, the controller sends signals to close the electromagnetic valves 32a and 32b and open the electromagnetic valves 28a and 28b so as to warm the treatment tub 10, and the molten paraffin is supplied again to the treatment tub 10 from the finally selected tank 18 of the tanks 18 and 18 equipped with the heaters so as to melt the solidified paraffin having penetrated into the tissue preparations.

By cooling the treatment tub 10 and supplying the molten paraffin, the solidification treatment and the melting treatment are conducted at least once for each of the tissue preparations, so that the tissue preparations treated by the paraffin-penetration treatment method of the present invention can be easily sliced after being embedded in paraffin and the sliced pieces can be well used for microscopic observation.

In case of using tissue preparations, e.g., skin, ischiadic nerve, which have not been degreased for a long time, if the solidification treatment and the melting treatment are not conducted as well as the conventional method, good sliced pieces cannot be obtained from the tissue preparations into which paraffin have merely penetrated.

The tissue preparations, which have been treated by the paraffin-penetration treatment method of the present invention, can be easily sliced by solidifying and re-melting the paraffin having penetrated into the tissue preparations, and the reason is considered that volume of the paraffin is reduced by the solidification treatment and increased by the melting treatment. Therefore, fat, etc. left in cells can be discharged outside by solidifying and re-melting the paraffin having penetrated into the cells, so that the cells can be sufficiently filled with the paraffin.

Cooling and solidifying the paraffin having penetrated into the tissue preparations may be performed in a state of immersing the tissue preparations in the molten paraffin, but a cooling rate of the tissue preparations can be improved by separating the tissue preparations from the molten paraffin.

In some kinds of tissue preparations, by cooling and solidifying paraffin at room temperature, preferably 0° C. or below (more preferably 0-5° C.), the paraffin penetration is accelerated, the tissue preparations can be easily sliced after being embedded in paraffin, and sliced pieces can be well used for microscopic observation.

Further, the solidification treatment and the melting treatment may be conducted once; in case of using tissue preparations into which paraffin can hardly penetrate, preferably the solidification treatment and the melting treatment are performed twice or more.

Note that, if the solidification treatment and the melting treatment are unnecessarily repeated, the time period for the paraffin-penetration treatment will be prolonged and effects will be saturated. Preferably, optimum number of repeating the solidification treatment and the melting treatment should be previously found by experiments.

After performing the paraffin-penetration treatment, the tissue preparations are taken out from the treatment tub 10, embedded in paraffin, and sliced by a microtome, so that sliced pieces for microscopic observation can be produced.

Note that, the temperature and pressure may be varied and the solutions may be agitated while treating the tissue preparations in the treatment tub 10 so as to accelerate processing speeds.

In the above described embodiment, the paraffin-penetration treatment method is performed in the apparatus having one treatment tub, but the method may be performed by immersing the baskets storing the tissue preparations into a plurality of the tanks storing the solutions and a plurality of the tanks equipped with heaters, which are serially arranged, in order, for prescribed time periods.

Example 1

A human skin was immersed in formalin and fixed as a tissue preparation. The tissue preparation was immersed in tanks, in which the solutions shown in TABLE 1 were stored, and treated under the conditions shown in TABLE 1.

In the ethanol treatments and the paraffin treatment steps shown in TABLE 1, pressurization and depressurization were repeated several times so as to accelerate the penetration into the tissue preparation. Conditions of the pressurization and the depressurization are also shown in TABLE 1.

TABLE 1

| TREATMENT STEP | SOLUTION | TEMPERATURE (° C.) | IMMERSING TIME (minute) | PRESSURE | AGITATION |
|---|---|---|---|---|---|
| 1 | ETHANOL 90% | 37 | 60 | PRESSURIZATION | YES |
| 2 | ETHANOL 95% | | | 35 (kPa) | |
| 3 | ETHANOL 99.5% | | | DEPRESSURIZATION | |
| 4 | ETHANOL 99.5% | | | −70 (kPa) | |
| 5 | ETHANOL 99.5% | | | | |
| 6 | ETHANOL 99.5% | | | | |
| 7 | ETHANOL 99.5% | | | | |
| 8 | XYLENE | | | ATMOSPHERIC PRESSURE | |
| 9 | XYLENE | | | ATMOSPHERIC PRESSURE | |
| 10 | XYLENE | | | ATMOSPHERIC PRESSURE | |
| 11 | PARAFFIN | 63 | | PRESSURIZATION | |
| 12 | PARAFFIN | | | 35 (kPa) | |
| 13 | PARAFFIN | | | DEPRESSURIZATION | |
| 14 | PARAFFIN | | | −70 (kPa) | |

Upon completing the treatment step 14, the tissue preparation, into which the paraffin had penetrated, was held in an atmosphere of −5° C. for 10 minutes, so that the molten paraffin in the tissue preparation was solidified.

Next, the tissue preparation, in which the paraffin was solidified, was re-immersed in the molten paraffin of 63° C. so as to melt the paraffin in the tissue preparation. Further, the tissue preparation, into which the paraffin penetrated again, was held in the atmosphere of −5° C. for 10 minutes so as to re-solidify the paraffin.

The solidification treatment and the melting treatment were repeated four times for the same tissue preparation.

The obtained tissue preparation was embedded in paraffin so as to form a block, and then the block was sliced by a microtome so as to form sliced pieces whose thickness was 3 μm.

According to observation, tissues and a border part between tissues and paraffin were not cracked, so that the sliced piece could be well used for microscopic observation.

Example 2

The paraffin-penetration treatment was performed as well as Example 1, but the temperature of the cooling atmosphere, which was used in Example 1, was room temperature (25° C.), the obtained tissue preparation was embedded in paraffin and formed into a block, and the block was sliced by the microtome.

In comparison with Example 1, it was difficult to slice the block, but a sliced piece, whose thickness was 3 μm, could be produced.

According to observation, a border part between tissues and paraffin were slightly cracked, but the sliced piece could be used for microscopic observation.

Example 3

The paraffin-penetration treatment was performed as well as Example 1, but the tissue preparation was ischiadic nerve obtained from a human body, the tissue preparation was embedded in paraffin and formed into a block, and the block was sliced by the microtome.

In comparison with Example 1, it was difficult to slice the block, but a sliced piece, whose thickness was 3 μm, could be produced.

According to observation, a border part between tissues and paraffin were slightly cracked, but the sliced piece could be used for microscopic observation.

Comparative Example 1

The paraffin-penetration treatment was performed as well as Example 1, but the solidification treatment and the melting treatment were not repeated (i.e., the treatment steps shown in TABLE 1 were executed until the step 14), the tissue preparation was embedded in paraffin and formed into a block, and the block was tried to be sliced by the microtome.

However, the block was hardly sliced by the microtome, and many cracks are formed in tissues and a border part between tissues and paraffin in a sliced piece, so the sliced piece could not be used microscopic observation.

Comparative Example 2

The paraffin-penetration treatment was performed as well as Comparative Example 1, but the tissue preparation was ischiadic nerve obtained from a human body, the tissue preparation was embedded in paraffin and formed into a block, and the block was sliced by the microtome.

However, the block was hardly sliced by the microtome, and many cracks are formed in tissues and a border part between tissues and paraffin in a sliced piece, so the sliced piece could not be used microscopic observation.

The invention claimed is:

1. An apparatus for performing a paraffin-penetration treatment, in which a dehydrated and degreased tissue preparation is immersed in molten paraffin so as to allow the paraffin to penetrate into the tissue preparation before embedding the tissue preparation in the paraffin, said apparatus, which is used in a process of producing the tissue preparation for microscopic observation, comprising:

penetration means for immersing the tissue preparation in the molten paraffin so as to allow the paraffin to penetrate into the tissue preparation;

solidification means for cooling and solidifying the paraffin, which has been allowed to penetrate into the tissue preparation by said penetration means; and a controller for controlling said penetration means and said solidification means so as to perform a solidification treatment, in which the tissue preparation is cooled and the molten paraffin which has been penetrated inside the tissue is solidified, and to perform a melting treatment, in which the tissue preparation is immersed in the molten paraffin again so as to melt the solidified paraffin having penetrated into the tissue preparation, wherein said solidification treatment and said melting treatment are conducted at least once for one tissue preparation.

2. The apparatus according to claim 1, wherein said solidification means solidifies the paraffin having penetrated into the tissue preparation in a state in which the tissue preparation is separated from the molten paraffin.

3. The apparatus according to claim 1, wherein the tissue preparation in which molten paraffin has been penetrated is cooled at room temperature or below.

4. The apparatus according to claim 3, wherein the temperature is 0° C. or below.

5. An apparatus for performing a paraffin-penetration treatment, in which a dehydrated and degreased tissue preparation is immersed in molten paraffin so as to allow the paraffin to penetrate into the tissue preparation before embedding the tissue preparation in the paraffin, said apparatus, which is used in a process of producing the tissue preparation for microscopic observation, comprising:

a treatment tub whose outer circumferential face is covered with a jacket;

a basket, in which the tissue preparation is stored, being accommodated in the treatment tub;

a pipe for supplying a cooling medium to the jacket via a first electromagnetic valve;

a pipe for discharging the cooling medium from the jacket via a second electromagnetic valve;

a pipe for supplying a heating medium to the jacket via a third electromagnetic valve;

a pipe for discharging the heating medium from the jacket via a fourth electromagnetic valve;

penetration means for immersing the tissue preparation in the molten paraffin so as to allow the paraffin to penetrate into the tissue preparation;

solidification means for cooling and solidifying the paraffin, which has been allowed to penetrate into the tissue preparation by said penetration means;

a controller for controlling said penetration means and said solidification means so as to perform a solidification treatment, in which the tissue preparation is cooled and the molten paraffin which has been penetrated inside the tissue is solidified, and a melting treatment, in which the tissue preparation is immersed in the molten paraffin again so as to melt the solidified paraffin having penetrated into the tissue preparation, wherein said solidification treatment and said melting treatment are conducted at least once for one tissue preparation; and said controller further controlling said first electromagnetic valve, said second electromagnetic valve, said third electromagnetic valve and said fourth electromagnetic valve so as to suitably supply the cooling medium and the heating medium to the jacket and to suitably discharge the same therefrom, whereby an inner space of said treatment tub is maintained at desired temperature.

* * * * *